(12) United States Patent
Johnson

(10) Patent No.: US 11,975,117 B2
(45) Date of Patent: May 7, 2024

(54) DOME LIGHT WITH SANITIZING FEATURES

(71) Applicant: Sam Johnson, Largo, FL (US)

(72) Inventor: Sam Johnson, Largo, FL (US)

( * ) Notice: Subject to any disclaimer, the term of this patent is extended or adjusted under 35 U.S.C. 154(b) by 438 days.

(21) Appl. No.: 17/410,144

(22) Filed: Aug. 24, 2021

(65) Prior Publication Data
US 2022/0062475 A1 Mar. 3, 2022

Related U.S. Application Data

(60) Provisional application No. 63/072,457, filed on Aug. 31, 2020.

(51) Int. Cl.
| | |
|---|---|
| *A61L 2/10* | (2006.01) |
| *B60Q 1/26* | (2006.01) |
| *B60Q 3/51* | (2017.01) |

(52) U.S. Cl.
CPC .............. *A61L 2/10* (2013.01); *B60Q 1/2611* (2013.01); *B60Q 3/51* (2017.02); *B01D 2259/804* (2013.01)

(58) Field of Classification Search
CPC .......... A61L 2/10; A61L 2/22; A61L 2202/14; A61L 2202/11; A61L 2202/25; B60Q 1/2611; B60Q 3/51; B60Q 3/20; B01D 2259/804
See application file for complete search history.

(56) References Cited

U.S. PATENT DOCUMENTS

| | | | |
|---|---|---|---|
| 10,639,393 B1 * | 5/2020 | Sustrick | A61L 2/10 |
| 10,835,091 B2 * | 11/2020 | Cawthon | E06B 11/08 |
| 11,802,699 B2 * | 10/2023 | Zhang | F24F 8/108 |
| 2016/0058933 A1 * | 3/2016 | Ballantyne | G06F 21/565 |
| | | | 210/85 |
| 2018/0118337 A1 * | 5/2018 | Viel | B64C 39/024 |
| 2018/0172264 A1 * | 6/2018 | Heuer | F21V 23/0485 |
| 2019/0316948 A1 * | 10/2019 | Karol | A61M 1/282 |
| 2021/0299303 A1 * | 9/2021 | Mullen | A61L 2/26 |
| 2021/0330847 A1 * | 10/2021 | Ou Yang | A61L 2/26 |
| 2022/0062475 A1 * | 3/2022 | Johnson | B60Q 3/51 |
| 2023/0177149 A1 * | 6/2023 | Ballantyne | G05B 15/02 |
| | | | 210/85 |

* cited by examiner

*Primary Examiner* — David A Vanore
(74) *Attorney, Agent, or Firm* — Weide & Miller, Ltd.

(57) ABSTRACT

A dome-style light is provided for vehicles or other environments and includes one or more sanitizing feature such as light elements and/or a disinfectant dispenser. The light elements may be UVC emitting lights. The disinfectant dispenser may include a container or tank of aerosol or liquid disinfectant. The light includes a control unit for controlling the lights and/or dispenser at certain times. The control unit may receive an output for one or more sensors, such as detectors, for detecting activity in the presence of the light, where the control unit may prevent the illumination of the light(s) or the dispensing of disinfectant when activity is detected. The light may be retrofit into a vehicle for use in disinfecting a vehicle.

20 Claims, 3 Drawing Sheets

DOME LIGHT WITH SANITIZING FEATURES

RELATED APPLICATION DATA

The present application claims priority to U.S. Provisional Application Ser. No. 63/072,457, filed Aug. 31, 2020, which application is incorporated by reference herein in its entirety.

BACKGROUND

The disclosed embodiments relate to lighting with built in sanitizing features. More specifically, the disclosed embodiments relate to original or aftermarket lighting that may be installed in a vehicle, home, or other environment to provide both light and sanitization to a space.

Many people are concerned about keeping areas clean. This becomes truer during periods where illnesses are present such as during flu season or during periods such as one currently being experienced, the Covid-19 pandemic. To prevent infection, increased cleaning may be performed in living spaces. However, some may wish to find ways to achieve increased cleaning and sanitization without increased efforts. Further, some areas, such as automobiles, may not be routinely cleaned, or at least sanitized, during a person's routine cleaning. Therefore, ways to increase cleanliness and/or sanitization.

SUMMARY OF THE INVENTION

Embodiments of the invention comprise a method and device for disinfecting one or more areas, such as the interior of a vehicle.

One embodiment of the invention is a dome-style light device which includes one or more sanitizing feature such as light elements and/or a disinfectant dispenser. The light may comprise a housing and, in some examples, a cover.

The light disinfecting elements may comprise one or more UVC emitting lights. The disinfectant dispenser may comprise a container or tank of aerosol or liquid disinfectant.

The device includes a control unit for controlling the lights and/or dispenser at certain times. The control unit may receive an output for one or more sensors, such as detectors, for detecting activity in the presence of the light, where the control unit may prevent the illumination of the light(s) or the dispensing of disinfectant when activity is detected.

The control unit may include a transceiver, permitting the control unit to communicate with one or more external devices, such as a user's mobile communication device. The control unit may receive input, such as programming or control instructions from the external device(s).

The device may be retrofit into a vehicle for use in disinfecting a vehicle.

Further objects, features, and advantages of the present invention over the prior art will become apparent from the detailed description of the drawings which follows, when considered with the attached figures.

DETAILED DESCRIPTION OF EMBODIMENTS

In the following description, numerous specific details are set forth in order to provide a thorough description of the various embodiments of the invention. It will be apparent, however, to one skilled in the art, that all of these specific details may not be required in every embodiment of the invention. In other instances, well-known features have not been described in detail so as not to obscure the various embodiments of the invention.

Figure 1A:
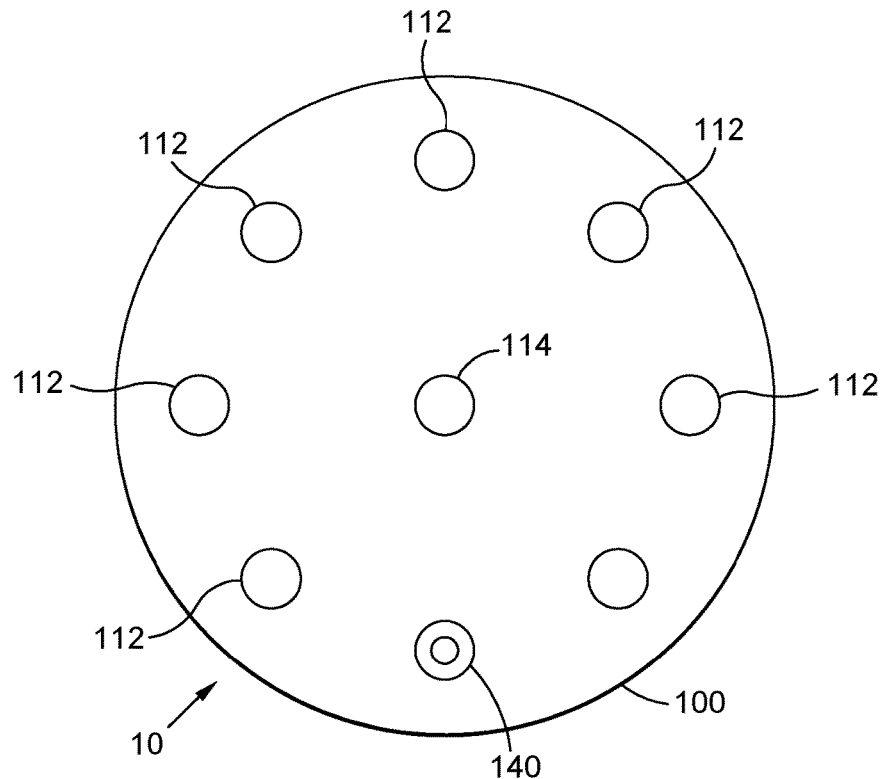
FIGS. 1A and 1B show a dome light with sanitizing features, according to one exemplary embodiment.
Figure 1B:
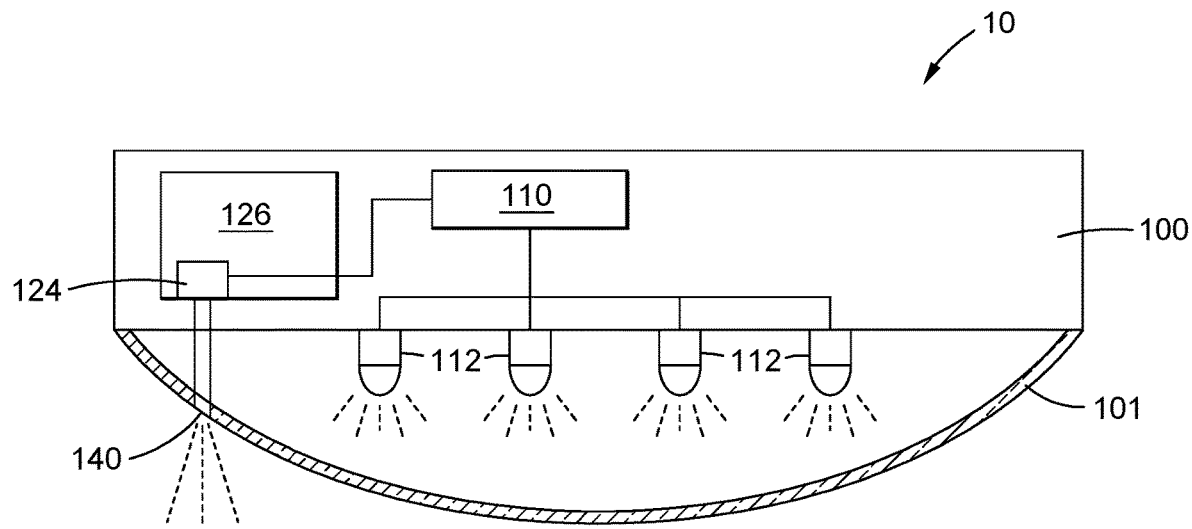

In one embodiment, a dome light is provided that includes one or more sanitizing features or devices. FIGS. 1A and 1B show an exemplary light 10 of the invention. As detailed below, in that one environment of use of the light 10 is inside a vehicle and the light may have a dome-shaped cover, the light may be referred to as a dome light 10. In one example, the dome light 10 may be configured to be installed as an aftermarket accessory in a vehicle. For instance, the dome light 10 may be installed to replace or compliment an original dome light in a vehicle. In other embodiments, the dome light 10 may be original equipment in a vehicle. The vehicle may be an automobile, an all-terrain vehicle, a recreational vehicle such as a motor home or travel trailer, a boat, or the like.

It should be noted that while the present embodiment is described in reference to a dome light for a vehicle, other applications are also applicable using the same principles disclosed herein. For example, a light with built-in sanitizers may be used in other environments and living spaces such as a replacement or original light for a desk lamp, a light in a room of a house, store, garage, workbench or apartment, etc.

The dome light 10 comprises a housing 100. The housing 100 may be circular in peripheral shape as shown in FIG. 1A, or may take on any other shape based on the application or vehicle in which the dome light 10 is to be placed. The housing 100 may be configured to be easily attached to a vehicle so as to be portable between many different vehicles (including, for example, a user's own vehicle and then a rental vehicle while travelling). That is, the housing 100 may comprises a vehicle attachment mechanism to easily attach to and detach from the vehicle. In some embodiments, the attachment mechanism may be a clip, a strap with a hook-and-loop fastener, or the like which may easily clip or attach to a sun visor, seat back, headboard, or other part of a vehicle. In other embodiments, the housing 100 might be attached to the vehicle (or other support) via one or more brackets or mounts, or via other types of fasteners (threaded fasteners, etc.)

In other embodiments, the housing 100 may be mounted in a more permanent fashion to the vehicle, such as being original equipment in a vehicle, or added as an aftermarket accessory to a vehicle to supplement or replace an existing vehicle dome light. The housing 100 may include or define one or more interior areas for housing components of the light, including an area for housing one or more light emitting elements as disclosed below, which elements might be covered by a generally transparent cover 101 (which cover may, as indicated above, be "dome" shaped, but might have various shapes) or the like, as best illustrated in FIG. 1B. In such a configuration, the housing 100 may be configured to be mounted so that the light emitting elements emit light in a particular direction, such as downwardly and/or outwardly away from the housing.

Figure 2:
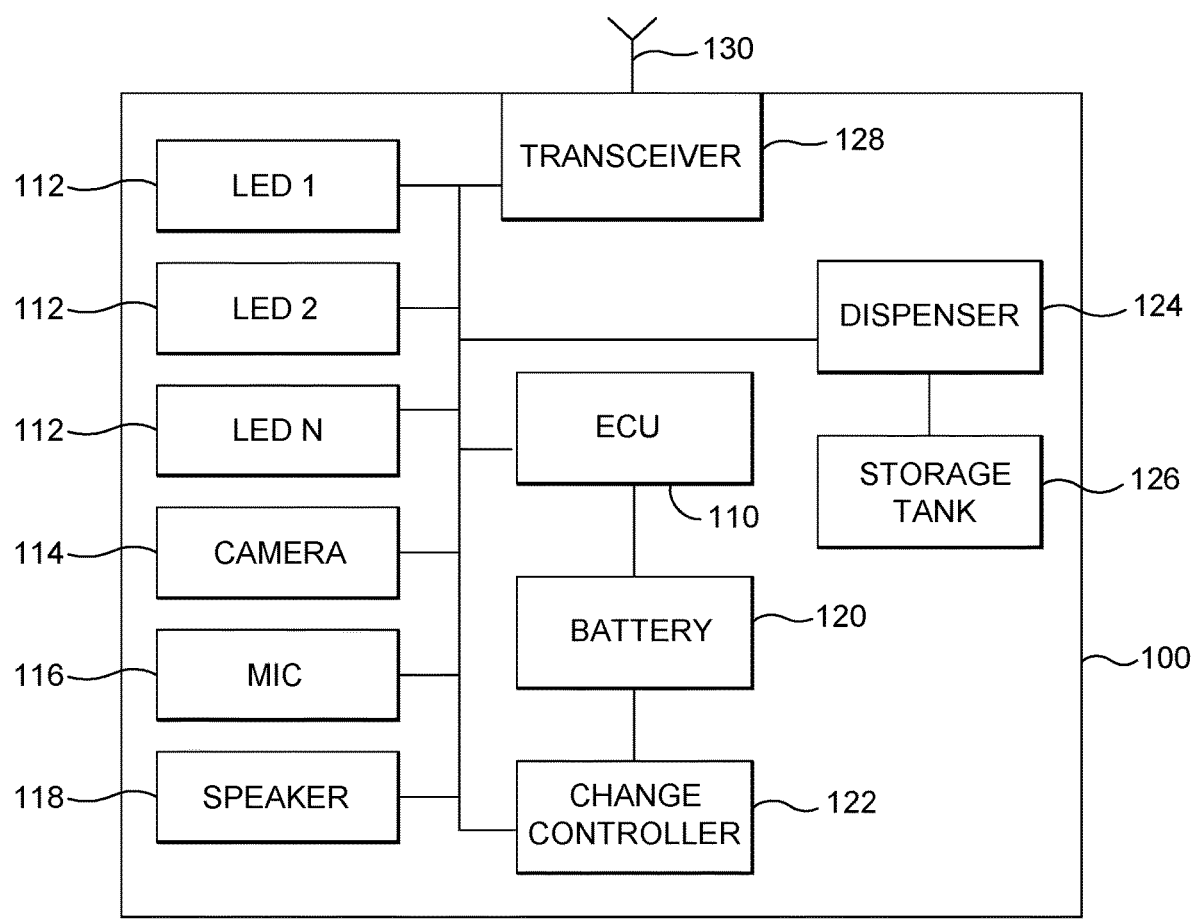
FIG. 2 shows a schematic of a dome light with sanitizing features, according to one exemplary embodiment.

Referring to FIG. 2, the dome light 10 may be considered a "smart" device in that the dome light comprises an electronic control unit ("ECU") 110. The ECU comprises a processor, and one or more memories storing machine readable instructions to control the operation of the dome light 10.

Further, the dome light 10 may be communicatively coupled or connected to one or more external devices (including, but not limited to external systems, including remote servers, laptops, tablets, desktop computers, iPhone or Android mobile phones, PDAs or other mobile communication devices, including mobile communication devices which run a compatible application, such as a control application) via a transceiver 128. The transceiver 128 may comprise one or more antennas 130 and may facilitate wireless communication through any number of wireless protocols now known or later developed. The ECU 110 may receive instructions from the external device(s) via the transceiver 128 and may also send information to the external device(s) via the transceiver. In other embodiments, the dome light 10 may also include a wired connection port of any suitable protocol to facilitate a wired connection to the vehicle and to interact with vehicle systems and features.

The dome light 10 may include various features mounted to or within the housing 100 which are controlled by the ECU 110. For example, the dome light 10 may comprise a plurality of lights, such as LED lights 112. The LED lights 112 may be configured to emit light at various wavelengths. For example, the LED lights 112 (or one or more of them) may emit light at one or more wavelengths of the visible light spectrum. The wavelengths emitted by the LED lights 112 may be alterable, or various ones of the LED lights 112 may emit light at different wavelengths. In some embodiments, the intensity of the light emitted from the LED lights 112 may be adjustable either manually or automatically (such as if someone is detected near the vehicle the LED wavelength would automatically adjust to, for example, 222 nm which is a safe wavelength while still performing the sanitation). In other embodiments, other wavelengths may be emitted by the LED lights 112 such as ultra-violet light or infrared light. In some embodiments one or more the LED lights 112 may be configured to emit UVC light as a way of disinfection. In some examples, one or more of the LED lights 112 may be configured to emit visible light and others may emit a sanitizing light, such as UVC light.

The LED lights 112 are connected to the ECU 110. The ECU 110 may control the operation of the LED lights 112 to change emitted wavelengths or intensity, and/or to turn on and off selected LED lights 112. The ECU may control the LED lights 112 based on instructions received from one or more external devices via the transceiver 128. For example, where both visible light and UVC light emitting LEDs are provided, the visible light LEDs might be activated when motion is sensed in the vicinity of the light 10, upon user input/activation, etc., while the UVC light emitting LEDs may, as detailed below, only be activated at certain times, including when no activity is detected in the vicinity of the light 10.

The dome light 10 may further comprise one or more cameras 114 or other image capture devices (including for capturing still images or video). Other input and output devices may be included such as a microphone 116 and speaker 118 through which a user may interact with the dome light 10 such as to give voice commands or to receive alerts. The devices are connected to the ECU 110. The ECU 110 controls the camera 114, microphone 116, and speaker 118 and may receive and store information received from the same. Additionally, the ECU 110 may transmit information to/from the camera 114, microphone, 116, and/or speaker 118 from/to the external device(s) via the transceiver 128. In some embodiments, the dome light 10 may interface via the transceiver 128 or a wired connection with vehicle input/output devices such as vehicle mounted cameras, speakers, microphones, etc.

In some embodiments, the dome light 10 may comprise a dispenser 124. The dispenser 124 may be controlled by the ECU 110 to emit a disinfectant spray (such as an aerosol or liquid disinfectant) that may be stored in a storage tank or other container 126 of the dome light 10. The storage tank 126 may have an access port to allow for refilling of the disinfectant stored in the storage tank 126. The dispenser 124 might comprise, for example, a pump (which might draw disinfectant from the tank, might push air into the tank to force the disinfectant out, might move a diaphragm to change the volume of the tank to force the disinfectant out, might open a valve which permits pressurized disinfectant in the tank to be released, etc.) for causing disinfectant to be dispensed from the tank 126, such as through a nozzle 140 (see FIG. 1B).

The dome light 10 may be powered by a battery 120. The battery 120 may be a rechargeable battery such as those that are known in the art. The dome light 112 may comprise a charge controller 122 with a charge port to connect to an external power supply to charge the battery 120 or to provide direct power to the dome light 10. In some embodiments, the charge controller 122 may be connected via wiring to the vehicle to receive power from the vehicle. In other embodiments, the housing 110 and/or the battery 120 and charge controller 122 may be removable to be charged at a remote location.

The dome light 10 may take on a variety of configurations to provide lighting to a vehicle (or other space) and also to disinfect the vehicle and/or items within the vehicle. An example describing a configuration for one method of use is shown in FIG. 3.

Figure 3:
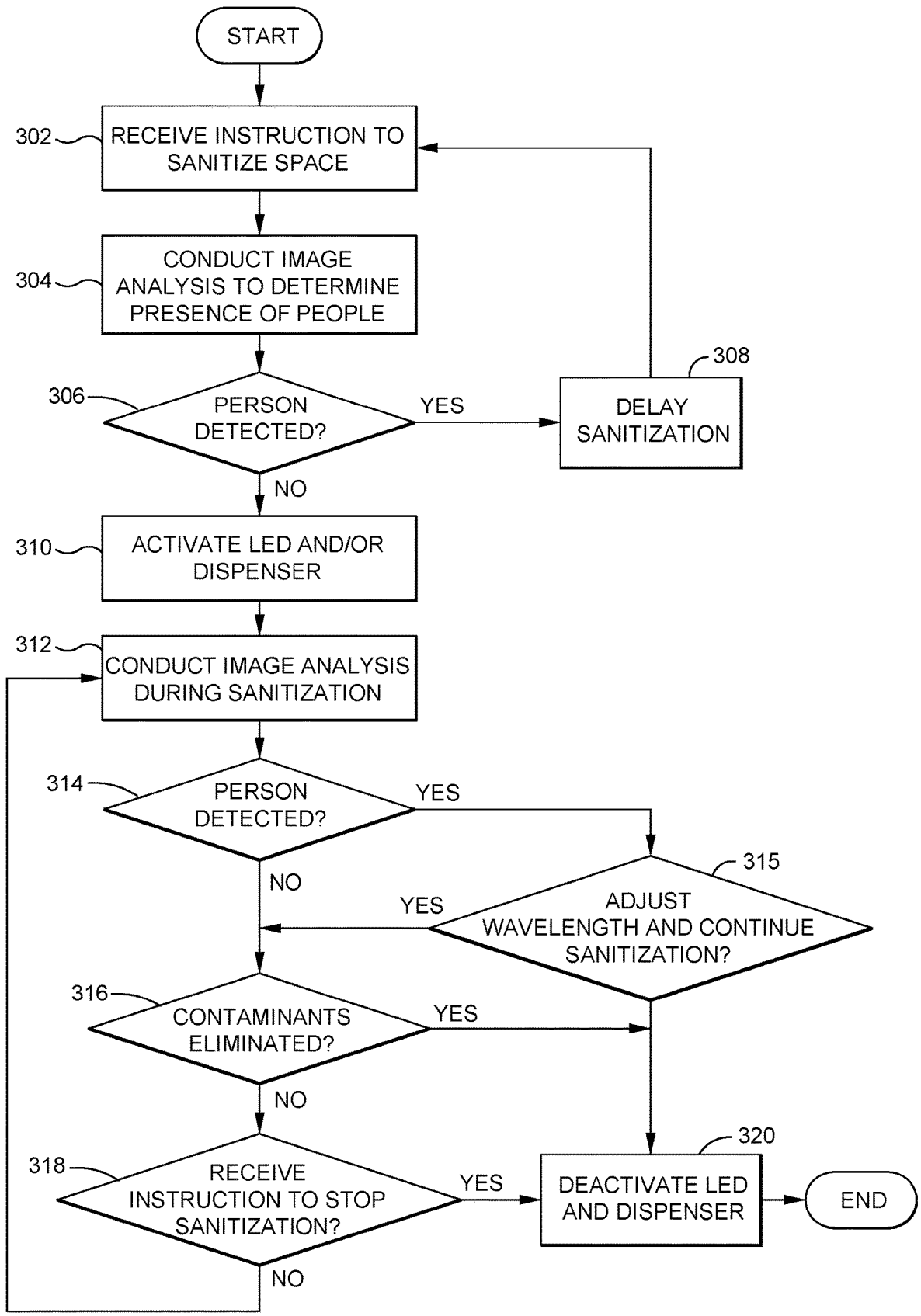
FIG. 3 shows a method of sanitizing using a dome light, according to one exemplary embodiment.

In FIG. 3, a method of using the dome light 10 for sanitization is described. The dome light 10 may be used to sanitize a vehicle or other space as described above. In step 302, the dome light 10 received instructions to sanitize the space, such as a vehicle. The instructions may be relayed to the ECU 110 via the transceiver 128 from the external device(s). For example, a mobile phone running an application may be used to initiate sanitization on the dome light 10, or be used to program the dome light 10 with specific operating instructions or parameters. For example, the ECU may store a set of instructions (e.g. such as via machine-readable code with associated data, such as where the data may also be stored in the memory and may be updated based upon input by a user to their mobile device, where different schedules may be stored and selected or created/modified, etc.) with a schedule indicating sanitization to be performed at a given time of day or may begin sanitation 5 minutes after each time the occupants of the vehicle have left the vehicle, or more precisely down to a compartment of the vehicle (e.g. rear passenger seats) once the compartment is unoccupied for 1 minute. In some embodiments, if the dome light 10 is programmed to perform sanitization at certain times, the time for a particular sanitization may be overridden if no activity was detected in the vicinity of the dome light 10 (such as inside the vehicle) since the last sanitization.

In step 304, the camera 114 is activated by the ECU 110 (or the ECU receives camera data from camera external to the dome light, such as cameras mounted inside or around the vehicle), and the ECU 110 monitors data received from the camera to detect activity/movement in the vicinity of the light 10, such as to determine whether a person is present in the vicinity of the dome light 10, such as within and/or near the vehicle (and/or as determined by other sensors, such as a motion sensor, the microphone 116 which detects sounds/speech, etc.). Because certain disinfectant sprays and the presence of UVC light are harmful to humans, the dome light 10 is configured to ensure that sanitation using such tools is done without people present. Thus, in step 306, if image analysis by the ECU 110 or external device(s) determines that a person (or such is determined by a motion sensor, detection of sound/speech by the microphone 116, etc.) is present based on the data received from the camera 114, the sanitization process may be delayed as shown in step 308. The process may begin again at step 302 after a given lapse of time, at a next scheduled sanitization time, or when instructions to begin sanitization are again received at the ECU 110.

If there is no person detected in step 306, the ECU activates one or more of the LED lights 112 to emit ultraviolet light such as UVC light to sanitize the vehicle and/items in the vehicle. Additionally or alternatively, the ECU activates the dispenser 124 to dispense disinfectant that is stored in the storage tank 126 into the vehicle to disinfect the vehicle and/or items in the vehicle.

During the sanitization process, the ECU 110 continues to receive data from the camera 114 (or external camera) and conducts image analysis on the data to monitor for the presence of any new person in the vehicle or surrounding area during sanitization, as shown in step 310. If a person is detected in step 314, the process proceeds to step 315. In step 315, the ECU 110 may be optionally programmed to automatically change the wavelength of the one or more LED lights 112 to emit a wavelength that is safe in the presence of humans. The sanitization process may then continue in step 316. Alternatively, the ECU 110 may be programmed to terminate upon detection of a person. In this case, the sanitization is terminated in step 320. This allows the process to operate safely even if a person enters the vehicle or vicinity around the vehicle after sanitization has begun. Additionally, the images from the camera 114 may be relayed to an external device, such as a user's mobile phone, via the transceiver 128 to monitor the sanitization process remotely (or at other times if desired).

In some embodiments, the ECU 110 may monitor image data from the camera 114 to determine whether contaminants have been sufficiently eliminated in step 316 (and/or other sensors might be used, including other types of image collection devices). The duration of the sanitization process may be based on the outcome of the analysis of the image data and/or might depend upon other factors such as the length of time since the last disinfecting cycle. When it is determined that the contaminants have been eliminated in step 316, the sanitization process ends in step 320. In another embodiment, the sanitization process may additionally/alternatively end when instructions to stop the sanitization process are received from an external device (e.g. from an instruction from a mobile phone connected to the dome light 10), via a scheduled stop time stored on the ECU 110, or the like, as shown in step 318. In step 320, the sanitization process ends by the ECU 110 deactivating the LED lights 112 and the dispenser 124.

As indicated above, in some embodiments, inputs from a remote device such as a mobile phone may be used to activate, control and/or program the dome light 10. In other embodiments, the ECU 110 might be pre-programmed and might be operable simply by turning one/powering the dome light 10. In some embodiments, a user might provide direct input to the dome light 10, such as by the microphone (voice command) or by the dome light 10 including one or more buttons or selectors. For example, the dome light 10 might include a slidable selector which permits a user to set the dome light 10 to implement one of two or more different pre-programmed sanitization schedules. In another embodiment, the dome light 10 might have an "auto"-mode, in which the dome light is configured to sanitize after activity is detected (and is no longer detected) the like.

The above described dome light 10 may thus have several useful applications for both providing visible light to an area as a traditional dome light as well as for safely disinfecting an area such as within a vehicle. An advantage to the dome light 10 and is location at or near the roof of the interior of a vehicle is that the dome light 10 is positioned to effectively disinfect the interior of the vehicle, including the seats, steering wheel, door handles, seat belts and other features that are thus generally below the dome light 10. Other modifications may also be implemented in addition to that described above.

For example, the housing 100 may be fitted with a motorized or non-motorized swivel allowing the housing to rotate. This may allow the housing to aim the dispenser 124 or one or more LED lights 112 to certain areas of the vehicle for selective sanitization. For example, if a taxi or ride share driver desires to disinfect a rear seat after a passenger exits the vehicle, the housing 100 may be moved so that only the rear seat is sanitized while the driver remains in the vehicle.

In some embodiments, the external device, such as the mobile device may receive data concerning a sanitization process such as duration, location (such as captured by GPS associated with the dome light 10 or other means), time, and camera image data for each sanitization session. The external device may maintain a log of sanitization events at the dome light, or other events. For example, such data might be provided to an application associated with a user's mobile communication device, such as to provide alerts when a long period of time has passed since a disinfecting process, to trigger an alert in the event a person is detected during a disinfecting process, to alert the user that the disinfecting solution is running low, etc.). Similar data might be provided to remote devices such as remote servers or computer, such as by multiple dome lights 10. Also, in some cases, the dome light 10 might be configured to communicate with systems of the vehicle, such as via a CANBUS, wherein the vehicle control system might be configured to activate or control the dome light 10. Of course, a single user might control multiple dome lights 10, such as through a single application—such as dome lights associated with more than one of their vehicles or a business's fleet of vehicles.

It will be understood that the above described arrangements of apparatus and the method there from are merely illustrative of applications of the principles of this invention and many other embodiments and modifications may be made without departing from the spirit and scope of the invention as defined in the claims.

What is claimed is:

1. A method of sanitizing an area comprising the steps of:
   determining, based upon one or more detectors of a dome light style sanitizing device located in said area, whether activity is occurring in the vicinity of said device;
   when activity is determined to not be occurring in the vicinity of said device, activating, via a processor configured to execute non-transitory machine-readable code stored in a memory device, a dispenser of disinfectant and a lighting device disposed on said housing, said dispenser connected to a storage tank configured to contain said disinfectant and said lighting device configured to emit UVC radiation.

2. The method of claim 1, wherein said area comprises the interior of a vehicle.

3. The method of claim 1, wherein said activation of said dispenser permits disinfectant to be dispensed from said storage tank.

4. The method of claim 1, wherein said one or more detectors comprise at least one of a motion sensor and a camera.

5. The method of claim 1, further comprising receiving, via a transceiver of said device, at least one instruction to activate said dispenser and said lighting device.

6. The method of claim 1, further comprising de-activating said dispenser and said lighting device in response to the detection of activity in the vicinity of said device.

7. The method of claim 1, comprising activating said dispenser and said lighting device for a determined period of time.

8. The method of claim 1, comprising programming said device to sanitize said area at a predetermined times and activating said dispenser and said light at said predetermined time unless activity is determined to be occurring in the vicinity of said device.

9. A vehicle-mountable sanitizing device comprising:
a housing;
means for mounting the housing to a vehicle;
a storage tank supported by said housing, said storage tank configured to store a disinfectant;
a dispenser configured dispense said disinfectant from said storage tank through at least one nozzle;
a lighting device disposed on the housing, said lighting device configured to emit UVC radiation;
an input device disposed on the housing for detecting movement in the vicinity of said device; and
an electronic control unit disposed within the housing, said electronic control unit comprising non-transitory machine-readable code stored in a memory device and executable by a processor, to cause said processor to:
activate said lighting device and/or said dispenser at one or more times when no movement is detected by said input device in the vicinity of said device; and
in response to input received from said input device indicating activity in the vicinity of said device, when said dispenser is activated, deactivating said dispenser to prevent emission of said disinfectant and when said lighting device is activated, deactivating said lighting device to prevent emission of UVC radiation.

10. The device of claim 9, wherein said one or more nozzles are configured to emit disinfectant in more than one direction and/or emit different amounts of disinfectant.

11. The device of claim 10, wherein said processor configured to, in response to input received from said input device, change at least one of the direction of said dispensing and the amount of disinfectant dispensed.

12. The device of claim 9, wherein said one or more lighting devices are configured emit UVC radiation in more than one direction and/or emit UVC radiation at more than one wavelength.

13. The device of claim 9, wherein said processor is configured to, in response said input received from said input device deactivate said lighting device by changing a wavelength of an output of said lighting device.

14. The device of claim 9, wherein said input device comprises at least one of an image capture device, a microphone and a motion detection device.

15. The device of claim 9, wherein said processor is further configured to deactivate said nozzle and said lighting device after a pre-determined amount of time following activation.

16. The device of claim 9, further comprising a communication transceiver for receiving one or more programming instructions from a mobile communication device.

17. The device of claim 9, further comprising a communication transceiver, wherein said processor activates said lighting device and/or said dispenser in response to an input from a remote mobile communication device.

18. The device of claim 9, further comprising at least one secondary lighting device, said secondary lighting device configured to emit visible light.

19. The device of claim 9, wherein said machine-readable code is configured to cause said processor to activate said lighting device and/or said dispenser at a first time, and at a second time unless said input device does not indicate activity in the vicinity of said device between said first time and said second time.

20. The device of claim 9, wherein said one or more times comprise a time after said input device detects activity in the vicinity of said device and said input device thereafter no longer detects activity in the vicinity of said device.

* * * * *